United States Patent [19]

Nakayama

[11] Patent Number: 5,420,356

[45] Date of Patent: May 30, 1995

[54] PROCESS FOR PRODUCING CYCLOBUTANONES

[75] Inventor: Yoshinori Nakayama, Ibaraki, Japan

[73] Assignee: Sumitomo Chemical Company, Limited, Osaka, Japan

[21] Appl. No.: 216,847

[22] Filed: Mar. 24, 1994

[30] Foreign Application Priority Data

Aug. 11, 1993 [JP] Japan .................................. 5-199379

[51] Int. Cl.$^6$ ............................................. C07C 45/45
[52] U.S. Cl. ................................................. 568/364
[58] Field of Search .......................................... 568/364

[56] References Cited

U.S. PATENT DOCUMENTS

| 4,028,418 | 6/1977 | van den Brink et al. | 568/364 |
| 4,064,174 | 12/1977 | Verbrugge | 568/364 |
| 4,216,172 | 8/1980 | Heine et al. | 568/364 |
| 4,284,821 | 8/1981 | Martin et al. | 568/364 |
| 4,691,052 | 9/1987 | Brandy et al. | 568/364 |

FOREIGN PATENT DOCUMENTS

| 2539048 | 3/1976 | Germany | 568/364 |
| 3045768 | 6/1981 | Germany | 568/364 |
| 59-12093 | 3/1984 | Japan | 568/364 |
| 1524682 | 9/1978 | United Kingdom | 568/364 |
| 1571581 | 7/1980 | United Kingdom | 568/364 |

*Primary Examiner*—James H. Reamer

[57] ABSTRACT

A process for producing cyclobutanones with industrial advantage is provided which comprises contacting an $\alpha$-haloacetyl halide with an ethylenic unsaturated compound in the presence of a dehydrohalogenating agent and a Lewis acid.

7 Claims, No Drawings

PROCESS FOR PRODUCING CYCLOBUTANONES

FIELD OF THE INVENTION AND RELATED ART STATEMENT

1. Field of the Invention

The present invention relates to a process for producing cyclobutanones.

Cyclobutanones represented by the formula

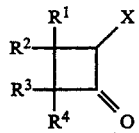

wherein $R^1$, $R^2$, $R^3$ and $R^4$ may be the same or different and each denotes a hydrogen atom or an alkyl or alkenyl group optionally substituted with at least one member selected from the group consisting of F, Cl and Br, provided that two of them may combine with each other to form a carbon ring; and X denotes F, Cl or Br, are known as useful intermediates for synthesizing pharmaceuticals and agricultural chemicals.

For example, cyclobutanones can be converted into cyclopropanecarboxylic acids through Favorskii rearrangement under an alkaline condition (Angew. Chem. Int. Ed. Engl. 27, 797 (1988)), which acids can be used as the carboxylic acid component of pyrethroid insecticides having a high insecticidal activity.

2. Related Art Statement

A known process for producing cyclobutanones comprises contacting an α,α-dihaloacetyl halide with an ethylenic unsaturated compound in the presence of a dehalogenating agent, such as zinc or tin (JP-B-59-12093).

However, α,α-dihaloacetyl halides are rather difficult to be available industrially. Moreover, to attain a good selectivity in the above process, the dehalogenating agent such as zinc or tin must be used in at least twice the molar amount of the α,α-dihaloacetyl halide and, to prevent a side reaction from occurring, the use of such specific solvents as dialkyl ethers or dialkyl ketones is required.

OBJECT AND SUMMARY OF THE INVENTION

The present inventor has made an extensive study to find an industrially advantageous process for producing cyclobutanones. As a result, he has found that cyclobutanones can be obtained in a high yield by using α-haloacetyl halides, which are easily obtainable industrially, without using α,α-dihaloacetyl halides and by reacting the α-haloacetyl halides with ethylenic unsaturated compounds in the presence of a dehydrohalogenating agent and a Lewis acid. The present invention has been attained on the basis of this finding.

DETAILED DESCRIPTION OF THE INVENTION

According to the present invention, there is provided a process for producing cyclobutanones represented by the formula

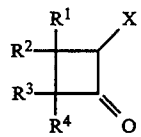

wherein $R^1$, $R^2$, $R^3$ and $R^4$ may be the same or different and each denote a hydrogen atom or an alkyl or alkenyl group optionally substituted with at least one member selected from the group consisting of F, Cl and Br, provided that two of them may combine with each other to form a carbon ring; and X denotes F, Cl or Br, which comprises reacting an α-haloacetyl halide represented by the formula

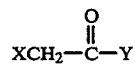

wherein X is the same as defined above and Y, which may be the same as or different from X, denotes F, Cl or Br, with an ethylenic unsaturated compound represented by the formula

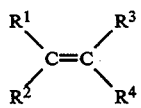

wherein $R^1$, $R^2$, $R^3$ and $R^4$ are the same as defined above, in the presence of a dehydrohalogenating agent and a Lewis acid.

The α-haloacetyl halide used in the present invention may be, for example, α-chloroacetyl chloride, α-bromoacetyl bromide, α-fluoroacetyl chloride and α-bromoacetyl chloride.

The ethylenic unsaturated compound may be those of the above-mentioned formula in which $R^1$ through $R^4$ are each a hydrogen atom or an alkyl or alkenyl group having about 1–20 carbon atoms and optionally substituted with F, Cl or Br. They include, for example, monoenes, such as ethene, propene, 1-butene, isobutene, cis-2-butene, trans-2-butene, 2-methyl-2-butene, 2,3-dimethyl-2-butene, 2-pentene, 2-methyl-2-pentene, 3-methyl-2-pentene, 2,3,4-trimethyl-2-pentene, 2-hexene, 3-hexene, 3-methyl-3-hexene, 2,5-dimethyl-3-hexene, 2-heptene, 3-heptene, 1-octene, 2-octene, 3-octene, 1-nonene, 1-decene, 1-undecene, 1-dodecene, 1-tetradecene, 1-pentadecene, 1-hexadecene, methylenecyclopropane, methylenencyclobutane, methylenecyclopentane, methylenecyclohexane, cyclopentene, cyclohexene, 1-methyl-1-cyclohexene, 1,2-dimethyl-1-cyclohexene, 3,3,6,6-tetramethyl-1-cyclohexene, cycloheptene, cyclooctene, 1,1,1-trifluoro-3-butene, 1,1,1-trifluoro-4-hexene, 1,1,1-trifluoro-5-methyl-4-hexene, 1,1,1-trichloro-3-butene, 1,1,1-trichloro-3-pentene, 1,1,1-trichloro-4-methyl-3-pentene, 1,1,1-tribromo-4-methyl-3-pentene, 1,1,2-trichloro-4-methyl-3-pentene, 1,1,2-tribromo-4-methyl-3-pentene, 1,1,1-trifluoro-2,2-dichloro-5-methyl-4-hexene and 1,1,1-trifluoro-2,3-dichloro-5-methyl-4-hexene; and conjugated or non-conjugated dienes, such as butadiene, 1,3-pentadiene, 2-methyl-2,4-pentadiene, 1,5-hexadiene, 2,4-hexadiene, 2,5-dimethyl-2,4-hexadiene, 1,7-octadiene, 2,6-octadiene, 3,5-octadiene, 1,3-cyclooctadiene, 1,1-dichlorobutadiene, 1,1-dibromobutadiene, 1,1-dichloro-1,3-pentadiene, 1,1- dichloro-4-methyl-1,3-pentadiene, 1,1-dibromo-4-methyl-1,3-pentadiene and 1,1,1-trifluoro-2-chloro-5-methyl-2,4-hexadiene.

The dehydrohalogenating agent used may be, for example, amines including tertiary amines, such as N,N-dimethylaniline, N,N-diethylaniline, N,N-di-n-propylaniline, N,N-diisopropylaniline, N,N-di-n-butylaniline, N,N-diisobutylaniline, N,N,2,4,6-pentamethylaniline, N,N-diethyl-2,4,6-trimethylaniline, N,N-dineopentylaniline, N,N-diethyl-p-toluidine, N,N-di-n-butyl-p-toluidine, N,N-dineopentyl-p-toluidine, triisobutylamine, trineopentylamine, N,N-diisobutylcyclohexylamine and N,N-dineopentylcyclohexylamine; and aromatic amines, such as 2,6-dimethylpyridine, 2,6-di-n-butylpyridine, 2,6-diisopropylpyridine and 2,4,6-trimethylpyridine.

Preferred among these amines are N,N-dialkyl-substituted anilines. Particularly preferred are N,N-dialkyl-substituted anilines in which each alkyl group has 1-6 carbon atoms, such as N,N-dimethylaniline, N,N-diethylaniline, N,N-di-n-propylaniline, N,N-diisopropylaniline, N,N-di-n-butylaniline, N,N-diisobutylaniline, N,N,2,4,6-pentamethylaniline, N,N-diethyl-2,4,6-trimethylaniline and N,N-dineopentylaniline.

The Lewis acid to be used is not particularly limited and may be any conventionally used Lewis acid.

Specific examples of the Lewis acid include zinc chloride, zinc bromide, stannic chloride, stannic bromide, cobalt chloride, cobalt bromide, antimony chloride, antimony bromide, bismuth chloride, bismuth bromide, iron chloride, iron bromide, aluminum chloride, aluminum bromide, titanium chloride, titanium bromide, phosphorus oxychloride, sulfur trioxide, and the chlorides, bromides and trifluoromethanesulfonates of rare earth elements, such as lanthanum, cerium and samarium, each being used alone or as a mixture thereof.

The ratio of the starting compounds to be used is not particularly limited, but it is, for example, about 1-20 moles of the ethylenic unsaturated compound to 1 mole of the α-haloacetyl halide, preferably about 2-10 moles of the ethylenic unsaturated compound to 1 mole of the α-haloacetyl halide.

The dehydrohalogenating agent is used in an amount of, for example, about 1-8 moles, preferably about 1-4 moles, more preferably about 1-1.8 moles per 1 mole of the α-haloacetyl halide.

The amount of the Lewis acid used is, for example, about 0.0001-1 mole, preferably about 0.001-0.8 mole, more preferably about 0.01-0.8 mole per 1 mole of the α-haloacetyl halide.

The solvent, which may be used as required, may be conventionally used ones, e.g. halogenated hydrocarbon solvents and hydrocarbon solvents. Preferred are those which have 1-10 carbon atoms, such as methylene chloride, 1,2-dichloroethane, chlorobenzene, dichlorobenzene, hexane, cyclohexane, toluene and xylene.

The amount of the solvent may be suitably selected. It is, for example, about 3-15 parts by weight relative to 1 part by weight of the α-haloacetyl halide.

By using the ethylenic unsaturated compound of the starting material in an amount of about 3-15 parts by weight relative to 1 part by weight of the α-haloacetyl halide, the reaction can be conducted without using a solvent.

The reaction can be conducted, for example, by placing an α-haloacetyl halide, an ethylenic unsaturated compound, a Lewis acid and optionally a solvent in a reactor under a nitrogen stream and then adding a dehydrohalogenating agent dropwisely thereto. The time of dropwise addition of the dehydrohalogenating agent is, for example, about 0.5-5 hours. After completion of the addition, the reaction mixture is further stirred for about 1-10 hours to complete the reaction.

The reaction temperature during and after the dropwise addition is, for example, about 20°-120° C., preferably 30°-100° C.

Though the reaction is usually conducted at atmospheric pressure, it may be conducted under an applied pressure depending on the boiling point of the starting compounds and of the solvent.

After completion of the reaction, water or an aqueous acid solution of hydrochloric acid, sulfuric acid, etc. may be added to the reaction mixture to dissolve the residual dehydrohalogenating agent and Lewis acid into an aqueous layer and to remove them.

The intended cyclobutanones may be extracted and isolated from the organic layer thus obtained. Alternatively, the organic layer may be distilled under normal or reduced pressure to recover the starting compounds remaining in the organic layer and simultaneously to obtain a concentrated solution of cyclobutanones. The concentrated solution can be used as it is for the next process step, for example, a step of deriving 2,2-dimethylcyclopropanecarboxylic acids therefrom.

According to the present invention, cyclobutanones can be obtained in a high yield and in an industrially advantageous way by using α-haloacetylhalides, which are easily available industrially, as the starting material.

DESCRIPTION OF THE PREFERRED EMBODIMENT

EXAMPLE 1

In a flask were placed 125 g of 1,2-dichloroethane, 67.3 g (0.8 mole) of 2,3-dimethyl-2-butene, 22.6 g (0.2 mole) of α-chloroacetyl chloride and 43.8 g (0.1 mole) of stannic bromide. Then 49.0 g (0.3 mole) of N,N,2,4,6-pentamethylaniline was added dropwisely to the resulting mixture over a period of 2 hours while heating the mixture at 60° C. under a nitrogen stream, and the reaction mixture was kept at 60° C. for further 3 hours.

After completion of the reaction, a large quantity of water was added into the flask to wash the reaction mixture, then the organic layer was collected by separation and analyzed by gas chromatography. The yield of 2-chloro-3,3,4,4-tetramethylcyclobutanone was 91% (29.2 g).

The organic layer was distilled to recover 51.6 g of 2,3-dimethyl-2-butene and simultaneously to obtain a concentrated liquid containing 2-chloro-3,3,4,4-tetramethylcyclobutanone.

REFERENTIAL EXAMPLE 1

The concentrated liquid obtained in Example 1 and 146 g of water were placed in a flash, then 72.8 g of a 30% aqueous NaOH solution was added dropwisely to the resulting mixture with stirring while keeping the temperature of the mixture at 30° C., and the reaction mixture was kept at 30° C. for further 5 hours.

The aqueous layer was collected by separation and 39.7 g of a 40% aqueous sulfuric acid solution was added thereto, whereby white crystals separated out (m.p.: 119°-120° C.). Then 50 g of toluene was added thereto to extract the white crystals. After washing with water, the toluene layer was collected by separation. The toluene layer contained 24.1 g of 2,2,3,3-tetramethylcyclopropanecarboxylic acid.

The toluene layer was placed in a flask, dehydrated by azeotropic distillation, and 0.1 g of pyridine was added. Then 25.2 g of thionyl chloride was added dropwisely to the toluene layer under a nitrogen stream while keeping the temperature in the flask at 50° C. After completion of the dropwise addition, the reaction mixture was kept at 50° C. for further 3 hours. The resulting toluene layer contained 24.1 g of 2,2,3,3-tetramethylcyclopropanecarboxylic acid chloride. The toluene layer was concentrated, and then distilled under reduced pressure to isolate a purified acid chloride (b.p.: 88° C. at 35 mmHg).

EXAMPLE 2

The experimental procedure was the same as in Example 1 except that 125 g of chlorobenzene was used in place of 1,2-dichloroethane, a mixture of 8.8 g (0.02 mole) of stannic bromide and 10.9 g (0.08 mole) of zinc chloride was used in place of 43.8 g of stannic bromide and 44.8 g (0.3 mole) of N,N-diethylaniline was used in place of N,N,2,4,6-pentamethylaniline.

The yield of 2-chloro-3,3,4,4-tetramethylcyclobutanone was 84% (27.0 g).

EXAMPLE 3

The experimental procedure was the same as in Example 1 except that 88.0 g (0.8 mole) of 2,5-dimethyl-2,4-hexadiene was used in place of 2,3-dimethyl-2-butene, a mixture of 10.9 g (0.08 mole) of zinc chloride and 8.8 g (0.02 mole) of stannic bromide was used in place of 43.8 g of stannic bromide and 44.8 g (0.3 mole) of N,N-diethylaniline was used in place of N,N,2,4,6-pentamethylaniline.

A mixture of 2-chloro-4,4-dimethyl-3-(2-methyl-1-propenyl)cyclobutanone and 2-chloro-3,3-dimethyl-4-(2-methyl-1-propenyl)cyclobutanone was formed in a yield of 72% (26.9 g).

Further, 69.3 g of 2,5-dimethyl-2,4-hexadiene was recovered and simultaneously a concentrated liquid containing a mixture of 2-chloro-4,4-dimethyl-3-(2-methyl-1-propenyl)cyclobutanone and 2-chloro-3,3-dimethyl-4-(2-methyl-1-propenyl)cyclobutanone was obtained.

REFERENTIAL EXAMPLE 2

The experimental procedure was the same as in Referential Example 1 except that the concentrated liquid obtained in Example 3 was used, the amount of water was changed to 116 g, the amount of 30% aqueous NaOH solution was changed to 57.6 g and the amount of 40% aqueous sulfuric acid solution was changed to 31.4 g.

The toluene layer thus obtained contained 20.3 g of 2,2-dimethyl-3-(2-methylpropenyl)cyclopropanecarboxylic acid.

The experiment was further continued in the same manner as in Referential Example 1 except for changing the amount of thionyl chloride to 18.0 g.

The resulting toluene layer contained 22.1 g of 2,2-dimethyl-3-(2-methylpropenyl)cyclopropanecarboxylic acid chloride.

About 80% of the isolated purified acid chloride (b.p.: 101°–105° C. at 20 mmhg) had a trans configuration.

COMPARATIVE EXAMPLE

The experimental procedure was the same as in Example 1 except that stannic bromide was not used. As a result, the intended 2-chloro-3,3,4,4-tetramethylcyclobutanone was not detected from the organic layer.

What is claimed is:

1. A process for producing cyclobutanones represented by the formula

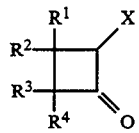

where $R^1$, $R^2$, $R^3$ and $R^4$ may be the same or different and each denotes a hydrogen atom or an alkyl or alkenyl group optionally substituted with at least one member selected from the group consisting of F, Cl and Br, provided that two of them may combine with each other to form a carbon ring; and X denotes F, Cl or Br, which comprises reacting an α-haloacetyl halide represented by the formula

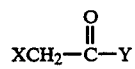

wherein X is the same as defined above and Y, which may be the same as or different from X, denotes F, Cl or Br, with an ethylenic unsaturated compound represented by the formula

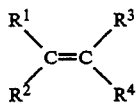

wherein $R^1$, $R^2$, $R^3$ and $R^4$ are the same as defined above, in the presence of an N,N-dialkyl-substituted aniline or triisobutylamine and a Lewis acid selected from the group consisting of zinc chloride, zinc bromide, stannic chloride, stannic bromide, cobalt chloride, cobalt bromide, antimony chloride, antimony bromide, bismuth chloride, bismuth bromide and the chlorides, bromides and trifluoromethanesulfonates of lanthanum, cerium and samarium, and mixtures thereof.

2. The process for producing cyclobutanones according to claim 1, wherein 0.0001–1 mole of said Lewis acid and 1–8 moles of said N,N-dialkyl-substituted aniline or said triisobutylamine are used per 1 mole of said α-haloacetyl halide.

3. The process for producing cyclobutanones according to claim 1, wherein said N,N-dialkyl-substituted aniline is selected from the group consisting of N,N-dimethylaniline, N,N-diethylaniline, N,N-di-n-propylaniline, N,N-diisopropylaniline, N,N-di-n-butylaniline, N,N-diisobutylaniline, N,N,2,4,6-pentamethylaniline, N,N-diethyl-2,4,6-trimethylaniline and N,N-dineopentylaniline.

4. The process for producing cyclobutanones according to claim 1, 2 or 3, wherein the α-haloacetyl halide is α-chloroacetyl chloride and the ethylenic unsaturated compound is 2,3-dimethyl-2-butene or 2,5-dimethyl-2,4-hexadiene.

5. A process for producing cyclobutanones represented by the formula

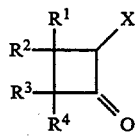

wherein $R^1$, $R^2$, $R^3$ and $R^4$ may be the same or different and each denotes a hydrogen atom or an alkyl or alkenyl group optionally substituted with at least one member selected from the group consisting of F, Cl and Br, provided that two of them may combine with each other to form a carbon ring; and X denotes F, Cl or Br, which comprises reacting an α-haloacetyl halide represented by the formula

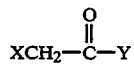

wherein X is the same as defined above and Y, which may be the same as or different from X, denotes F, Cl or Br, with an ethylenic unsaturated compound represented by the formula

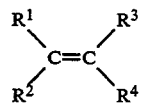

wherein $R^1$, $R^2$, $R^3$ and $R^4$ are the same as defined above, in the presence of a tertiary amine or aromatic amine dehydrohalogenating agent and a Lewis acid selected from the group consisting of zinc chloride, zinc bromide, stannic chloride, stannic bromide, cobalt chloride, cobalt bromide, antimony chloride, antimony bromide, bismuth chloride, bismuth bromide, iron chloride, iron bromide, aluminum chloride, aluminum bromide, titanium chloride, titanium bromide, phosphorous oxychloride, sulfur trioxide and the chlorides, bromides and trifluoromethanesulfonates of lanthanum, cerium and samarium, and mixtures thereof.

6. The process for producing cyclobutanones according to claim 5, wherein 0.0001–1 mole of said Lewis acid and 1–8 moles of said dehydrohalogenating agent are used per 1 mole of said α-haloacetyl halide.

7. The process for producing cyclobutanones according to claim 5 or 6, wherein the α-haloacetyl halide is α-chloroacetyl chloride and the ethylenic unsaturated compound is 2,3-dimethyl-2-butene or 2,5-dimethyl-2,4-hexadiene.

* * * * *